(12) United States Patent
Andrews

(10) Patent No.: US 11,110,190 B1
(45) Date of Patent: Sep. 7, 2021

(54) CURRENCY BILL DISPENSER WITH RADIATION STERILIZATION

(71) Applicant: David Scott Andrews, Berkeley, CA (US)

(72) Inventor: David Scott Andrews, Berkeley, CA (US)

( * ) Notice: Subject to any disclaimer, the term of this patent is extended or adjusted under 35 U.S.C. 154(b) by 0 days.

(21) Appl. No.: 17/320,085

(22) Filed: May 13, 2021

Related U.S. Application Data

(60) Provisional application No. 63/024,463, filed on May 13, 2020.

(51) Int. Cl.
*A61L 2/10* (2006.01)
*A61L 2/26* (2006.01)

(52) U.S. Cl.
CPC .............. *A61L 2/10* (2013.01); *A61L 2/26* (2013.01); *A61L 2202/11* (2013.01); *A61L 2202/14* (2013.01)

(58) Field of Classification Search
CPC .......... A61L 2/10; A61L 2/26; A61L 2202/11; A61L 2202/14
See application file for complete search history.

*Primary Examiner* — Nicole M Ippolito
*Assistant Examiner* — Hanway Chang
(74) *Attorney, Agent, or Firm* — Barry Choobin; Patent 360

(57) ABSTRACT

A currency bill dispenser that can disinfect the currency bill as the currency bill travels within the currency bill dispenser. The currency bill dispenser can include multiple UV-C lamps arranged on both sides of the currency bill. The intensity of the UV-C radiations at the currency bill can be increased by the use of collimating semi-cylindrical reflectors.

4 Claims, 4 Drawing Sheets

CURRENCY BILL DISPENSER WITH RADIATION STERILIZATION

CROSS-REFERENCE TO RELATED APPLICATIONS

This application claims priority to the U.S. provisional patent application Ser. No. 63/024,463, filed on May 13, 2020, which is incorporated herein by reference in its entirety.

FIELD OF INVENTION

The present invention relates to a currency bill dispenser, and more particularly the present invention relates to a currency bill dispenser that can disinfect the currency bills before dispensing.

BACKGROUND

Paper currency is a potential vector of transmissible diseases and a public health risk. As the paper currency is exchanged between different hands, it carries pathogens shredded from a hand of a giver of paper currency to the receiver of paper currency. Different pathogens including bacteria, fungi, yeast, viruses, and like can be easily transmitted from an infected hand through the paper currency. The material of the US paper currency bills provides a good surface area for the pathogens to reside and spread. Highly infective transmissible diseases, such as COVID-19 have raised concerns about the spreading of infections through paper currency. As a patient infected with COVID-19 could pass on COVID-19 through handling banknotes and using them to buy things, the World Health Organization (WHO) advised people to use contactless payments.

In the absence of proper disinfection of paper currency, people generally defer the use of paper currency. A growing number of businesses and individuals worldwide have stopped using the paper currency in fear that the paper currency, handled by tens of thousands of people over their useful life, could be a vector for the spreading COVID-19. Even though contactless payments may be an ideal solution, it is not tenable in the short term to avoid banknotes in most parts of the world, starting with the United States. Cash is used everywhere in small-scale transactions, everything from buying bread in bakeries to leaving a tip.

As such, there is a desire for a simple and inexpensive, yet effective apparatus to sanitize the paper currency at the point of sale or distribution

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a currency bill dispenser that can disinfect the currency bill using UV-C radiations.

It is another object of the present invention that the currency bill dispenser is portable and easy to use.

It is still another object of the present invention that the currency bill dispenser is economical to manufacture.

It is a further object of the present invention to prevent the spread of infection through currency bill.

It is still a further object of the present invention to make the currency bill safe to use.

In one aspect, disclosed is a currency bill dispenser having an input to receive a currency bill, the currency bill travels through a disinfection chamber having low-pressure Mercury vapor UVGI lamps or UV-C LED arrays for being exposed to the UV-C radiation for predetermined duration to disinfect the currency bill and the disinfected currency bill can be dispensed through an outlet of the currency bill dispenser.

In one aspect, a suitable number of reflectors can be used to increase the intensity of the UV-C radiations to which the currency bill is exposed.

In one aspect, the speed of the currency bill travel within the currency bill dispenser can be manipulated to achieve the desire predetermined duration of UV-C exposure.

In one aspect, the disclosed currency bill dispenser can include one or more trays to receive a collection of currency bill and one currency bill can be pulled from the bundle or the collection of currency bills and the one currency bill at a time can pass through the disinfection chamber. In one case, the different trays can include currency bills of different denominations and the desired number of currency bills of desired denominations can be dispensed by the currency bill dispenser.

In one aspect, the disinfection chamber can include an upper plate and a lower plate separated by suitable spacers. The mid portions of the upper plate and the lower plate can form a kill passage through which the currency bill can pass through. The mid portions of the upper plate and the lower plate can include concave arc shape or parabolic reflectors arranged lengthwise and side-by-side having collimating effect wherein the reflected UV-C rays can collimate and focused on the currency bill. Adjacent to the reflectors can be tubes of UV-c lamps or lens of UV LED arrays mounted to the upper plate and the lower plate. Suitable number of UV-C LED arrays combined with sapphire crystal can irradiate the kill passage i.e., currency bill and the reflectors.

These and other objects and advantages of the embodiments herein and the summary will become readily apparent from the following detailed description taken in conjunction with the accompanying drawings

BRIEF DESCRIPTION OF DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
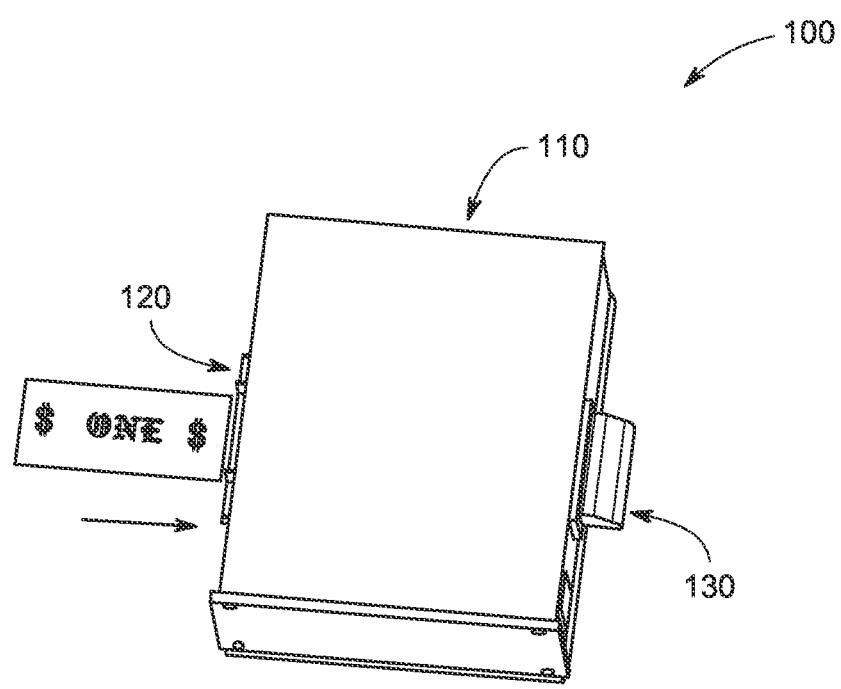
FIG. 1 is a perspective view of the currency bill dispenser, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a currency bill dispenser that can disinfect the currency bill using UV-C radiations. The currency bill dispenser can receive the currency bill through an inlet and travel within the currency bill dispenser for a predetermined duration and then can be dispensed out through an outlet of the currency bill dispenser. The currency bill dispenser can include a source of UV-C radiations. In one case, the source of UV-C radiations can be a low-pressure mercury-vapor UVGI lamp that can generate UV-C radiations in 250-270 nm ranges, and more preferably at 253.7 nm. Alternatively, UV-C LED arrays can also be used, wherein the number and position of the UV-C LED arrays can be adjusted for desired threshold of radiation exposure. It is to be understood that radiations other than UV-C radiations having microbiocidal actions can also be used without departing from the scope of the present invention. Suitable sapphire crystals can also be provided through which the UV-C radiations from the UV-C LED arrays can pass through and irradiate the currency bill. For example, four UV-C LED arrays, each having seven LEDs of suitable capacity, such as 50 mw can be provided. The Light can pass through 3"×2" sapphire crystal window irradiating the kill passage of the disinfection chamber.

In one exemplary embodiment, the currency bill dispenser can use 2 pairs of UVGI lamps i.e., four lamps, each lamp having two tubes. The two lamps can be provided on opposite sides of the currency bill and the tubes of the UV-C lamps can extend upto the middle portion of the upper and lower plate. As the currency bill passes through a disinfection chamber, the currency bill can be directly exposed to the UV-C radiations from all sides. The UV-C light from eight tubes can directly impinge the currency bill. The intensity of the UV-C radiation on the surface of the currency bill can be increased using the reflectors.

In one exemplary embodiment, the disclosed currency bill dispenser can include one or more trays to receive a collection of currency bill and one currency bill at a time can be pulled from the bundle or the collection of currency bill and the one currency bill can pass through the disinfection chamber. Generally, a user can either feed one bill at a time which is disinfected by passing through the kill passage of the disinfection chamber or the user can put a bundle of currency bills in the tray and the currency bill dispenser can pull one currency paper at a time from the tray and disinfect the currency bill and the disinfected currency bill can then be dispensed from an outlet. More than one tray can also be provided in which currency bills of different denominations can be placed is separate trays. A user can specify the amount and the dispenser can retrieve currency bills from the trays and move the currency bills through the disinfection chamber and dispenses through the outlet.

Referring to FIG. 1 which shows an exemplary embodiment of the currency bill dispenser 100 having an outer enclosure 110. As can be seen in FIG. 1, the currency bill dispenser 100 is compact that can be easily placed at a counter or table, such as a counter at the point of sale. The enclosure can have an inlet 120 for receiving the currency bill and an outlet 130 for dispensing the disinfected currency bill. A user rather than handling money directly to another person can simply insert the currency bill in the disclosed currency bill dispenser and the other person can receive the disinfected currency bill from the dispenser. Suitable batteries can also be used to power the disclosed currency bill dispenser making it truly portable. A person desiring to receive a payment, such as in a restaurant can simply carry and place the disclosed currency bill dispenser on a table. The customer can then insert the currency one by one in the inlet of the dispenser. In case, a tray is provided, multiples currency bills can be together kept in the tray of the dispenser.

Figure 2:
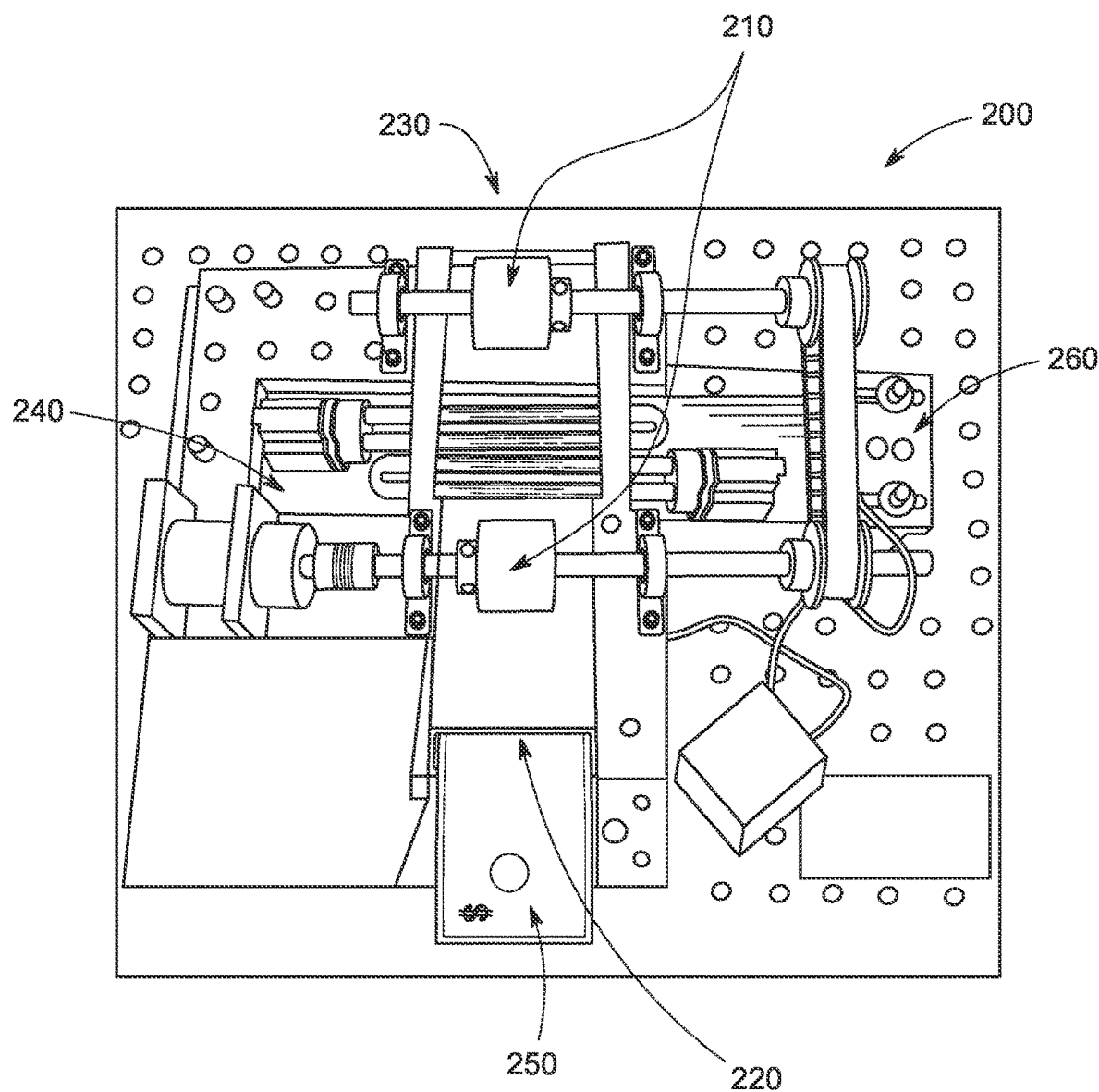
FIG. 2 shows the inner components of the currency bill dispenser including the UV-C lamps or UV-C LED arrays and lower reflector plate, according to an exemplary embodiment of the present invention.

Referring to FIG. 2 which shows the inner components of the disclosed currency bill dispenser 200. Suitable rollers 210 can be provided to move the currency bill between an inlet 220 and outlet 230. A disinfection chamber 240 traverses the path of the currency bill travel between the inlet and the outlet. The currency bill passes through the disinfection chamber and gets disinfected. FIG. 2 shows a currency bill 250 that is being received into the dispenser 200. The currency bill 250 can then pass through the disinfection chamber 240 that is traverse mounted in the enclosure. The disinfection chamber is formed by a pair of reflector plates one above another separated by suitable spacers. FIG. 2 shows the bottom plate 260 while the upper plate is removed for clarity.

Figure 3:
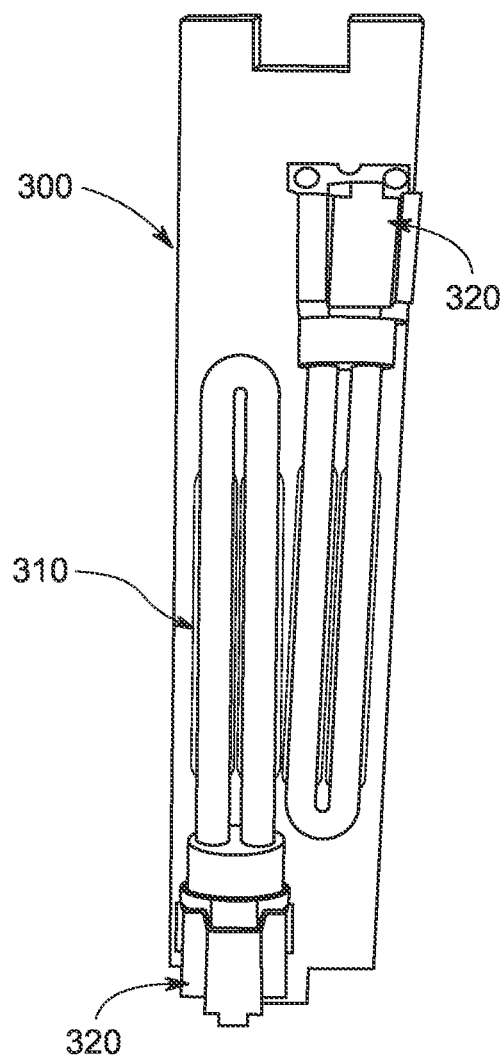
FIG. 3 shows the lower reflector plate of the two reflector plates of the disinfection chamber, the lower reflector plate having two of the four UV-C lamps on opposite ends and arc shape collimating cavities or parabolic reflectors in the mid portion, according to an exemplary embodiment of the present invention.

FIG. 3 shows an exemplary embodiment of the reflector plate 300. The mid-portion of the reflector plate 300 having a reflective area 310. The reflective area 310 is formed by concave arc shape cavities (parabolic reflectors) arrange side-by-side and lengthwise. The arc shape of cavities allows for a collimating effect wherein the UV-C rays upon reflected by the arc shape cavities can irradiate the currency bill sandwiched between the reflective areas of the upper plate and the lower plates. This produces high-intensity areas of irradiation on the currency bill that can provide the desired degree of disinfection in a short duration of time. The focused UV-C radiation may also slightly heat the exposed area of the currency bill thus adding to the kill rate of the pathogens on the currency bill. The reflective areas of the upper plate and the lower plate forms a kill passage in the path of the travel of the currency bill between the inlet and the outlet. The currency bill can pass through this kill passage and between the reflective areas of the upper plate and the lower plate.

Each the upper plate and the lower plate can have UV-C lamps. FIG. 3 shows the lower plate having two UV-C lamps 320 on opposite ends of the lower plate 300 and arranged offset to each other. Each UV-C lamp can have two tubes that irradiate the kill passage between the reflective surfaces 310. The tubes extends upto and above the reflective areas and light from the eight tubes of four lamps can irradiate the currency bill directly. The tubes can be about 4 mm from the currency bill and produce highly focused radiation reaching the disinfecting threshold within very short exposure duration. It is to be understood that the UV-C lamps can be replaced by UV-C LEDs. Additionally, any other radiation source can be used that can generate radiations for disinfecting the currency bill. The currency bill while traveling through the disinfection chamber gets disinfected and comes out through the outlet. The duration for which the currency bill is exposed to the UV-C radiations depends upon the travel rate of the currency bill. Slower is the travel rate of the currency bill, more is the time the currency bill is exposed to the UV-C radiations. The travel rate of the currency bill can be adjusted for desired speed and disinfection. Suitable controls can be provided to turn the dispenser on and off. Moreover, controls can be provided to adjust the speed of the dispenser. Indicators and stops can be provided for balancing the disinfection and speed of the currency bill travel.

Figures 4, 5:
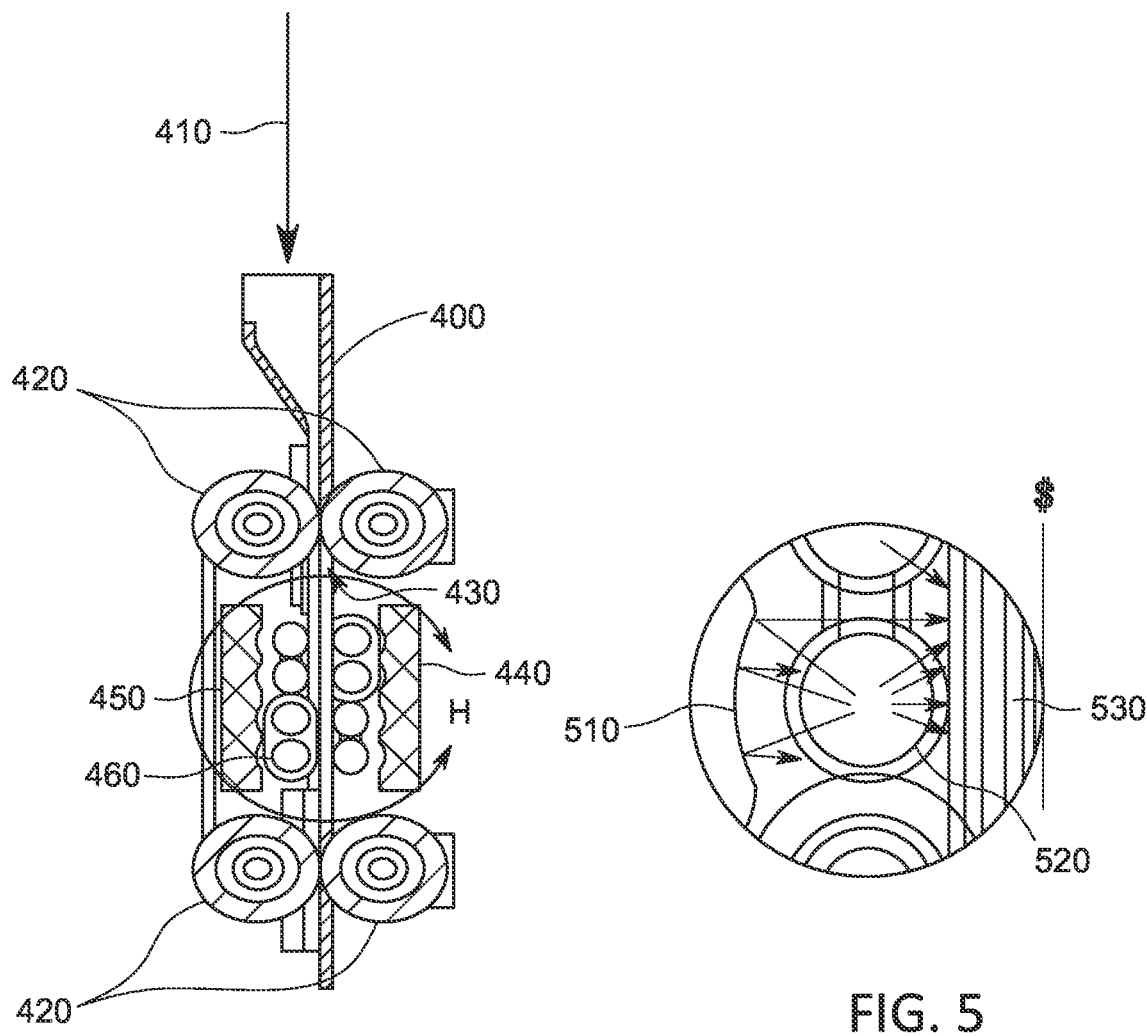
FIG. 4 is a sectional view showing the rollers, disinfection chamber having UV-C lamp tubes and arc shape cavities (parabolic reflectors) in the upper plate and the lower plate, according to an exemplary embodiment of the present invention.
FIG. 5 shows the reflection of UV-C rays from the UV-C lamp tube reflected by arc shape cavities (parabolic reflectors) in the mid portion of the upper and lower plates, according to an exemplary embodiment of the present invention.

Referring to FIG. 4 which is a sectional view showing a channel 400 that opens in the inlet 410 for receiving the currency bill. Two pair of rollers 420 can also be seen that moves the currency bill between an inlet and outlet. The rollers 420 can be operated by suitable motor. The area shown by H is referred herein as the kill passage. The currency bill from the inlet can travel into the kill passage by the rollers 420 and between the UV-C lamp tubes 460. FIG. 4 shows the upper plate 440 and the lower plate 450 both having arc shape cavities in the mid-portions. The UV-C radiations from the UV-C lamp tubes can irradiate the currency bill directly and the reflected UV-C rays from the arc shape cavities also indirectly irradiate the currency bill. FIG. 5 shows the reflection of the UV-C rays from the UV-C lamp tubes 520 and reflected by the arch shape cavities 510 or parabolic reflectors. The UV-C rays from the lamp tubes or the currency bill falling on the parabolic reflectors 510 reflects off of the parabolic reflectors can be roughly collimated (since the center of the eight light emitting tubes is in the focal line of the eight arc-shape parabolic reflectors) and directed back toward the currency bill. The disinfecting UV-C rays hits in the same position along the long axis of the currency bill from the top and bottom. It is to be understood that the UV-C lamps can be replaced by the UV-C LED arrays which works by the same mechanism and the reflected UV-C rays from the UV-C LED arrays can similarly reflected by the arc cavities towards the currency bill. UV-C LED arrays being lower in cost, generates less heating, and having longer life compared to UV-C lamps can be preferred over the UV-C lamps.

In embodiments, the number of UV-C LED arrays can be constant and limited variation can be bought by turning the UV-C LED arrays on and off. However, the speed the currency bill travels through the kill passage can be adjusted to ensure delivery of minimum threshold dose of disinfection radiations on the currency bill. Also, an optimal dose trading off against cost and speed is used so that currency bills can move faster enhancing cost effectiveness without sacrificing sterilization effectiveness. In one exemplary embodiment, the dispenser can also include a light shielding at inlet and outlet that prevents the leakage of UV-C.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:
1. A disinfecting currency bill dispenser comprising:
an enclosure having an inlet and an outlet for currency bill; and
a disinfection chamber having an upper plate and a lower plate separated by spacers, wherein midportion of the upper plate and the lower plate forms a kill passage through which the currency bill passes through, the midportion of each the upper plate and the lower plate having a plurality of concave arc shape cavities arranged lengthwise and side-by-side to form reflective area, the reflective area configured to focus reflected radiations on the currency bill sandwiched between the midportions of the upper plate and the lower plate, each the upper plate and the lower plate comprises a plurality of radiation source configured to irradiate the midportions of the upper plate and the lower plate.
2. The disinfecting currency bill dispenser according to claim 1, wherein the radiation source is UV-C LED array configured to produce UV-C radiations.
3. The disinfecting currency bill dispenser according to claim 1, wherein the plurality of rollers drive the currency bill between the inlet and the outlet and though the kill passage.
4. The disinfecting currency bill dispenser according to claim 1, wherein radiation source is UV-C lamp, the UV-C lamp comprising tubes that extend over the reflective area.

* * * * *